United States Patent [19]
Kirschner et al.

[11] Patent Number: 5,759,852
[45] Date of Patent: *Jun. 2, 1998

[54] EXPRESSION VECTOR CONTAINING PL6M PROMOTER AND TAT32 RIBOSOME BINDING SITE AND HOST CELLS TRANSFORMED THEREWITH

[75] Inventors: Richard J. Kirschner; John Edward Mott; Frances M. Eckenrode, all of Kalamazoo; David Paul Brunner, Portage, all of Mich.

[73] Assignee: Pharmacia & UpJohn Company, Kalamazoo, Mich.

[*] Notice: The term of this patent shall not extend beyond the expiration date of Pat. No. 5,510,256.

[21] Appl. No.: 266,908

[22] Filed: Jun. 27, 1994

Related U.S. Application Data

[62] Division of Ser. No. 13,828, Feb. 2, 1993, abandoned, which is a continuation of Ser. No. 562,861, PCT/US91/04565, filed Jul. 2, 1991, abandoned.

[51] Int. Cl.$^6$ .................. C07H 21/04; C12N 1/21; C12N 15/73
[52] U.S. Cl. .................. 435/320.1; 435/252.8; 536/24.1
[58] Field of Search .................. 435/252.3, 69.1, 435/69.7, 252.33, 172.1; 536/24.1, 24.2; 935/22, 23, 33, 39, 38, 41, 43, 44, 45, 73

[56] References Cited

U.S. PATENT DOCUMENTS

| | | | |
|---|---|---|---|
| 4,874,702 | 10/1989 | Fiers et al. | 435/172 |
| 5,182,196 | 1/1993 | Allet et al. | 435/69.5 |
| 5,206,353 | 4/1993 | Berger et al. | 536/23.4 |

FOREIGN PATENT DOCUMENTS

| | | | |
|---|---|---|---|
| PCT/US90/01367 | 4/1989 | WIPO | C07K 13/00 |
| PCT/US89/03267 | 2/1990 | WIPO | C07H 15/12 |
| WO 90/01035 | 2/1990 | WIPO | C07H 15/12 |

OTHER PUBLICATIONS

Gerald Preibisch, et al., "Unexpected translation initiation within the coding region of eukaryotic genes expressed in *Escherichia coli*", Gene 72:179–186, 1988.

R. A. Fisher, et al., Nature, 331, pp. 76–78 (1988).

Remes et al., "Adenosine 5'-triphosphate leakage does not cause abortive infection of bacteriophage T7 in male *Escherichia coli*", J. Bacteriol. 143(2): 1054–1056, Aug. 1980.

Schauder et al., "Inducible expression vectors incorporating the *Escherichia coli* atpE translational initiation region", Gene 52(2–3): 279–283, 1987.

Gorski et al., "The stability of bacteriophage T4 gene 32 mRNA: A 5'leader sequence that can stabilize mRNA transcripts", Cell 43(2): 461–469, 1985.

Lautenberger et al., "High level expression in *Escherichia coli* of the carboxy-terminal sequences of the avian myelocytomatosis virus (MC29) v–myc protein", Gene 23(1): 75–84, 1983.

Hanecak, R., et al. (1984), "Expression of a cloned gene segment of poliovirus in *E. coli*: Evidence for autocatalytic production of the viral proteinase," Cell 37:1063–1073;.

Ivanoff, L., et al. (1986), "Expression and site-specific mutagenesis of the poliovirus 3C protease in *E. coli*," Proc. Natl. Acad. Sci. USA 83:5392–5396;.

Grepinet, O., et al. (1988), "Nucleotide sequence and deletion analysis of the xylanase gene (xynZ) of *Colostridium thermocellu*." J. Bacteriol. 170:4582–4588;.

Halling, S. and Smith, S., (1985), "Expression in *E. coli* of multiple products from a chimaeric gene fusion: Evidence for the presence of procaryotic translational control regions within eucaryotic genes," Bio/Technology 3:715–720; and.

Arias, C., et al. (1986),. "Synthesis of the outer–capsid glycoprotein of the simian rotavirus SA11 in *E. coli*," Gene 47:211–219 (1986).

*Primary Examiner*—Douglas W. Robinson
*Assistant Examiner*—Amy T. Nelson
*Attorney, Agent, or Firm*—James D. Darnley, Jr.; Debbie K. Wright

[57] ABSTRACT

Disclosed are expression vectors useful as vectors in recombinant methods to facilitate expression of exogenous genes in *E. coli*. Specifically, the disclosed expression vector has the following elements in operable linkage: the PL6m promoter, the TAT32 ribosome binding site and a gene encoding a heterologous polypeptide. Also disclosed are *E. coli* host cells transformed with this expression vector.

6 Claims, No Drawings

1

EXPRESSION VECTOR CONTAINING PL6M PROMOTER AND TAT32 RIBOSOME BINDING SITE AND HOST CELLS TRANSFORMED THEREWITH

CROSS REFERENCE TO RELATED APPLICATIONS

This application is a divisional application of U.S. Ser. No. 08,013,828, filed Feb. 2, 1993, now abandoned; which is the national stage of PCT/US91/04565, filed Jul. 2, 1991; which is a continuation application of U.S. Ser. No. 07/562, 861, filed Aug. 6, 1990, now abandoned.

FIELD OF THE INVENTION

This invention relates to expression of recombinant DNA sequences. More particularly, it relates to expression of DNA sequences encoding soluble CD4 (sCD4) polypeptides in microbial hosts.

BACKGROUND OF THE INVENTION

CD4, a normal membrane component of the T4 lymphocyte, binds gp120, an envelope glycoprotein of the human immunodeficiency virus (HIV). This RNA virus, which is responsible for acquired immune deficiency syndrome (AIDS) in humans, uses CD4 as its receptor for infection (Klatzmann, D., et al. (1984) "Selective tropism of lymphadenopathy associated virus (LAY) for helper-inducer T lymphocytes." Science 225:59-63). CD4 has 4 extracellular domains (Maddon, P., et al. (1985) "The isolation and nucleotide sequence of a cDNA encoding the T cell surface protein T4: A new member of the immunoglobulin gene family." Cell 42:93–104). A soluble molecule including some or all of these domains is referred to as sCD4. The two N-terminal domains of CD4 appear to be the most important for gp120 binding and proteins which incorporate this gp120 binding capability have been proposed as potential therapeutics for AIDS because they may target the protein to the virus, to HIV-infected cells, or to other species that might have exposed gp120 (Hussey, R., et al. (1988) "A soluble CD4 protein selectively inhibits HIV replication and syncitium formation." Nature 331:768–81; Deen, K., et al. (1988) "A soluble form of CD4 (T4) protein inhibits AIDS virus infection." Nature 331:82–84; Traunecker, A., et al. (1988) "Soluble CD4 molecules neutralize human immunodeficiency virus type 1." Nature 331:84–86; Berger, E., et al. (1988) "A soluble recombinant polypeptide comprising the amino-terminal half of the extracellular region of the CD4 molecule contains an active binding site for human immunodeficiency virus." Proc. Natl. Acad. Sci. U.S.A. 85:2357–2361). The determinants for high affinity binding of gp120 are in domain 1, residues 1–109 of CD4 (Arthos, J., et al. (1989) "Identification of the residues in human CD4 critical for the binding of HIV." Cell 57:469481).

sCD4-PE40 is such a potential therapeutic agent for the treatment of AIDS. (Chaudhary, V., et al. (1988) "Selective Killing of HIV-Infected Cells by Recombinant Human CD4-Pseudomonas Exotoxin Hybrid Protein." Nature 335:369–372). This hybrid protein consists of an N-terminal methionine (amino acid 1) followed by the first two domains of CD4 (178 amino acids), several linker amino acids, and the last two domains of Pseudomonas exotoxin A (amino acids 253–613 of the toxin). The resulting protein contains 545 amino acids and has a calculated molecular weight of approximately 59,200 daltons. Amino acids 2–110 in sCD4-PE40 (Chaudhary, supra) correspond to residues 3–111 in the cDNA sequence of Maddon, supra, except that residue 3 of the Maddon sequence should be lysine, and residues 1–109 (domain 1) of Arthos, supra. The gene for sCD4-PE40 has the sequence reported by Chaudhary, supra except that the codons that correspond to the N-terminal portion of the protein have been modified as described for sCD4-183 in PCT Application No. PCT/US90/01367, and codon 179, corresponding to Ala, is GCT rather than GCG.

Upon expression of sCD4-PE40 in $E.$ $coli$, we have found a major contaminant which is immunologically-related to sCD4-PE40 and has a molecular mass of approximately 50,000 daltons. This protein has the N-terminal sequence Met-Leu-Val-Phe-Gly-Thr-Ala- which corresponds to the C-terminal 449 residues of sCD4-PE40, i.e., beginning with Leu$^{97}$ (preceded by a methionine). The 50,000 dalton protein results from internal initiation within domain 1 of sCD4; a UUG codon down-stream of potential Shine-Dalgarno sequences is read as an initiation codon by f-Met-tRNA. Since the contaminant is closely related to the full length sCD4-PE40 product, it has similar biochemical properties. Accordingly, it co-purifies with the desired product and may interfere with the oxidation and folding of sCD4-PE40 to its biologically active conformation.

Among the potential causes investigated for the impurity is internal initiation. A gene including the above-described region of domain 1 with the potential for internal initiation may generate an impurity with an N-terminal Met-Leu-Val-Phe-Gly-Thr-Ala- sequence. Such internal initiation could result from translating a sCD4-containing gene in many prokaraytic organisms, including but not limited to $E.$ $coli$. Since proteins including sCD4 components are potential human drugs, it is desirable to eliminate the cause of the contaminating protein.

Four sequence-related features appear to positively favor translation initiation in prokaryotes. First, the preferred initiation codon is AUG. GUG and UUG can function as initiation codons although at only about 10 and 1 percent of the frequency of AUG, respectively. (Hershey, J. (1987) Protein Synthesis. In "$Escherichia$ $coli$ and $Salmonella$ $typhimurium$: Cellular and Molecular Biology". F. C. Neidhardt, et al., eds. (American Society for Microbiology: Washington, DC) p.613–641.) These codons are recognized by f-Met-tRNA as the site where amino acid polymerization is to begin (Gold, L. (1988) "Posttranscriptional Regulatory Mechanisms in $E.$ $coli$." Ann. Rev. Biochem. 57:199–233.)

The second feature that favors prokaryotic initiation is the Shine-Dalgarno sequence, e.g. 5'-UAAGGAGGUGA-3', a sequence in the mRNA which is complementary to the 3' terminal sequence of 16s rRNA, such that base pairs can be formed to stabilize the initiation complex. (Shine, J., and Dalgarno, L. (1974) "The 3' terminal sequence of $E.$ $coli$ 16s ribosomal RNA: Complementarity to nonsense triplets and ribosome binding sites." Proc. Natl. Acad. Sci USA 71:1342–1346; Steitz, J., and Jakes, K. (1975) "How ribosomes select initiator regions in mRNA: Base pair formation between the 3' terminus of 16s rRNA and the mRNA during initiation of protein synthesis in $E.$ $coli$." Proc. Natl. Acad. Sci. USA 72:4734–4738.) A variety of sequences which retain complementarity to the 16s RNA can function in this role. Shine-Dalgarno-like sequences, usually include GGAG or GAGG, and typically are located about 5–13 bases upstream of the initiation codon for most effective initiation. (Gold, L., supra.)

The third feature is a region which facilitates ribosome binding and initiation. A preferred pattern of nucleotides spanning at least –20 to +13 bases about the initiation codon of many $E.$ $coli$ genes has been detected by in vitro analysis of ribosome protected sequences (Steitz, J., supra) and by statistical analysis (Stormo, G., et al. (1982) "Characterization of translational initiation sites in *E. coli*." Nucleic Acids Res. 10:2971–2996; Schneider, T., et al. (1986) "Information Content of Binding Sites on Nucleotide Sequences." J. Mol. Biol. 188:415–431). Additionally, translation reinitiation can occur if a translational start signal overlaps (Oppenheim, D., and Yanofsky, C. (1980) "Translational Coupling During the Expression of the Tryptophan Operon of *Escherichia Coli*." Genetics 95:785–795) or follows one of the translational stop signals. (Steitz, J. (1979) "Genetic signals and nucleotide sequences in messenger RNA." In "Biological Regulation and Development. 1. Gene Expression.") Such reinitiation does not require a Shine-Dalgarno sequence and differs from the intragenic initiation discussed herein.

The fourth feature is the absence of significant mRNA secondary structure in the initiation codon region that might block the necessary annealing events with the 16s RNA or the initiator tRNA (Gold, L. (1988), supra).

The presence of potential translation initiation points can be identified in several ways. First, the sequencing of the N-terminus of immunoreactive peptides should yield methionine for peptides resulting from initiation although in some cases, methionine aminopeptidase can remove methionine leaving the adjacent residue in the sequence at the N-terminus (Waller, J. (1963) "The NH$_2$-terminal residue of the proteins from cell-free extracts of *E. coli*." J. Mol. Biol. 7:483–496; Ben-Bassat, A., et al. (1987) "Processing of the initiation methionine from proteins: Properties of the *E. coli* methionine aminopeptidase and its gene structure." J. Bacteriol. 169:751–757). In that case, one must rely on the gene sequence to determine if the terminal amino acid was encoded with an adjacent codon capable of initiating translation. Codons which direct the insertion of the N-terminal Met can be AUG, GUG or UUG (Gold, L., supra). Secondly, one can analyze the gene for sequences approximating a good initiation region. Many of these sequences are not functional. (Stormo, G., and Schneider, T., supra). Translation initiation points can be found through "footprinting" or "toeprinting" experiments in which regions of the mRNA to which ribosomes bind either are protected from nuclease digestion or block the elongation of a primed, reverse-transcribed DNA copy. (Gold, L., supra.)

Intragenic ribosome initiation sites have been identified in a number of genes. Following expression in *E. coli* of poliovirus 3C protease, initiation at the AUG of codon 27 gave rise to significant levels of an unstable internal initiation product (Hanecak, R., et al. (1984) "Expression of a cloned gene segment of poliovirus in *E. coli*: Evidence for autocatalytic production of the viral proteinase." Cell 37:1063–1073; Ivanoff, L., et al. (1986) "Expression and site-specific mutagenesis of the poliovirus 3C protease in *E. coli*." Proc. Natl. Acad. Sci. USA 83:5392–5396). Furthermore, expression of xylanase in *E. coli* was accompanied by the production of a species apparently initiating at GUG, codon 471. (Grepinet, O., et al. (1988) "Nucleotide sequence and deletion analysis of the xylanase gene (xynZ) of *Clostridium thermocellum*." J. Bacteriol. 170:4582–4588.) Translation initiation within the porcine parvovirus structural protein B occurs at internal initiation sites, with at least two of these internal initiation peptides produced at higher levels than the full length recombinant protein. (Hailing, S., and Smith, S. (1985) "Expression in *E. coli* of multiple products from a chimaeric gene fusion: Evidence for the presence of procaryotic translational control regions within eucaryotic genes." Bio/Technology 3:715–720.) Finally, expression of a simian rotavirus glycoprotein in *E. coli* generated an apparent product of internal initiation at a level similar to that of the full length molecule. (Arias, C., et al. (1986) "Synthesis of the outer-capsid glycoprotein of the simian rotavirus SA11 in *E. coli*." Gene 47:211–219.) It has been proposed that commercial production can be facilitated by removing internal initiation sites through mutagenesis (Hailing, S., supra).

Once the cause of the impurity has been determined to be internal initiation, a method of eliminating the internal initiation needs to be developed.

INFORMATION DISCLOSURE

As discussed above, several intragenic ribosome initiation sites have been identified. Initiation at the AUG of codon 27 gave rise to significant levels of an unstable internal initiation product following poliovirus 3C protease expression in *E. coli*. See, e.g., Hanecak, R., et al. (1984) "Expression of a cloned gene segment of poliovirus in *E. coli*: Evidence for autocatalytic production of the viral proteinase." Cell 37:1063–1073 and Ivanoff, L., et al. (1986) "Expression and site-specific mutagenesis of the poliovirus 3C protease in *E. coli*." Proc. Natl. Acad. Sci. USA 83:5392–5396. *E. coli* expression of xylanase was accompanied by the production of a species initiating at GUG. See, e.g., Grepinet, O., et al. (1988) "Nucleotide sequence and deletion analysis of the xylanase gene (xynZ) of *Clostridium thermocellum*." J. Bacteriol. 170:4582–4588. Translation initiation within the porcine parvovirus structural protein B occurs at internal initiation sites. See, e.g., Halling, S. and Smith, S. (1985) "Expression in *E. coli* of multiple products from a chimaeric gene fusion: Evidence for the presence of procaryotic translational control regions within eucaryotic genes." Bio/Technology 3:715–720. Halling and Smith suggest that mutagenesis could remove internal initiation sites. Simian retrovirus glycoprotein expression in *E. coli* also generated a product of internal initiation. See, e.g., Arias, C., et al. (1986) "Synthesis of the outer-capsid glycoprotein of the simian rotavirus SA11 in *E. coli*." Gene 47:211–219 (1986). None of these references mention CD4 proteins.

SUMMARY OF THE INVENTION

The present invention provides DNA sequences that eliminate internal translation initiation and do not change the amino acid sequence from genes containing portions of sCD4. More specifically, the modified sequence comprises:

```
5' GATCATCAAGAACCTGAAGATCGAAGACTCTGATACCTACATCTGTGAAGTTGAAGACCAGAAAGAAGAA
   TAGTTCTTGGAGTTCTAGCTTCTGAGACTATGGATGTAGACACTTCAACTTCTGGTCTTTCTTCTT

GTTCAACTGCTGGTGTTTGGTCTGACTGCTAACTCTGACACTCACCTGC
   CAAGTTGACGACCACAAACCAGACTGACGATTGAGACTGTGAGTGGACGA 5'
```

This sequence may be modified by various codon substitutions, deletions, additions or replacements. All such allelic variations and modifications resulting in a sCD4 protein in which internal translation initiation has been eliminated are included within the scope of this invention.

The present invention further provides recombinant DNA molecules which do not support internal initiation of sCD4. The present invention also provides host cells transformed with these recombinant DNA molecules.

The present invention also provides methods of eliminating internal initiation of sCD4 which comprises substituting base sequences for the Shine-Dalgarno-like sequences that precede the codon of amino acid 96 of sCD4 and/or modifying codon 96 or other codons which can be recognized for translation initiation.

The term "Shine-Dalgarno-like sequences" as used herein means sequences with complementarity to the 3' end of 16s rRNA and which could be used as a ribosome binding site. These can include but are not limited to GGAG, GAGG, AGGAGGT, GGAGG, and AAGGAGG.

The term "sCD4" refers to any protein or hybrid molecule that includes sequences related to those in T cell CD4 and is capable of binding to gp120, the external subunit of the HIV envelope glycoprotein. Such molecules are exemplified in Chaudhary, V., supra; Klatzmann, D., supra; Smith, D., supra; Fisher, R., supra; Hussey, R., supra; Deen, K., supra; Traunecker, A., supra; Berger, E., supra; Capon, D., et al. (1988) "Designing CD4 immunoadhesions for AIDS therapy." Nature, 337:525–531; and Till, M., et al. (1988) "HIV-infected cells are killed by rCD4-ricin A chain." Science 242: 1166–1168; European Patent Application No. 0,331,356. The term "hybrid molecule" refers to a molecule that contains functional components derived from two independent molecule species. The independent molecule species can be used in whole or in part to produce the "hybrid molecule".

The term "host cell" as used herein means any procaryotic cell capable of being transformed with the modified DNA sequence encoding the first domain of an sCD4 molecule wherein internal initiation expression has been eliminated without altering the amino acid sequence of the sCD4, including but not limited to E. coli.

DETAILED DESCRIPTION OF THE INVENTION

The present invention is based upon the discovery that proteins made from genes that include the CD4 sequence in its cDNA form can make additional polypeptides because of an intragenic nucleotide sequence which favors translation initiation. The invention is thus directed to a novel method for preventing such initiation, particularly comprising a modified sequence which minimizes the potential for internal initiation.

sCD4-PE40 is a four domain hybrid protein. It consists of N-terminal methionine, the first two domains of CD4 (178 amino acids), several linker amino acids, and the last two domains of Pseudomonas exotoxin A (amino acids 253–613 of the toxin). The resulting protein contains 545 amino acids and has a calculated molecular weight of approximately 59,200 daltons. See Chaudhary, V., supra.

A variety of lower molecular weight species cross-reacting with antibodies to sCD4 have been found by Western Blot analysis in a variety of E. coli stains producing sCD4-PE40. The major contaminant has a molecular weight of approximately 50,000 daltons and represented 5–20% of the level of sCD4PE40 in isolated inclusion bodies. Although such a species could result from errors in biosynthesis, e.g., frameshifting or termination, it seemed more likely to represent a proteolytic fragment. To test this hypothesis, it was necessary to identify the putative clip site in order to develop approaches for eliminating the protease (s) responsible for the proteolysis.

The impurity protein was characterized by N-terminal sequence analysis following isolation by electroblotting from SDS-PAGE or Reversed-Phase HPLC. The amino acid sequence of the impurity lacked the first 96 residues of sCD4-PE40; it began with N-terminal methionine and continued with the sequence starting at residue 97. The apparent molecular weight of 50,000 daltons observed on SDS-PAGE was in good agreement with the calculated molecular weight of 48,375 daltons for such a fragment of sCD4-PE40 comprising residues 96–545. In view of our original hypothesis, the presence of N-terminal methionine on the protein was surprising in that there are no known mechanisms for generating the identified sequence from the intact protein by proteolysis.

Protein synthesis in E. coli is initiated with N-formyl methionine. The N-terminal methionine is usually deformylated as the nascent peptide chain is elongated. Furthermore, depending on the adjacent amino acids, a methionyl amino peptidase often removes the N-terminal methionine. The cleavage is inhibited by the adjacent lysine in sCD4-183 and sCD4-PE40. The presence of methionine at the N-terminus of the impurity and the observed composition indicated that the impurity was not a proteolytic fragment but resulted from internal initiation at amino acid-96.

For initiation of protein synthesis, an initiation codon (usually AUG) is required. The presence of a Shine-Dalgarno-like sequence enhances the efficiency of initiation. To generate the observed impurity, an initiation codon must be present at a position corresponding to amino acid 96. The codon corresponding to Leu$^{96}$ is UUG. One of six codons specifying leucine, UUG is rarely found in the mRNA of highly expressed E. coli genes and the corresponding tRNA is found in low abundance. UUG is read, although infrequently (at <1% of normal initiation), by the f-Met-tRNA as an initiation codon. For this unusual initiation to occur, an upstream ribosome binding site is required. Inspection of the sequence encoding the impurity revealed three good Shine-Dalgarno-like sequences only five, eight and twenty nucleotides upstream of the UUG. Thus, internal translation was a reasonable explanation for the presence of a subsequence of sCD4-PE40 beginning with Met-Leu$^{97}$.

A modified sCD4-PE40 can be constructed in which the leucine codon has been changed from UUG to CUG and the GGAGG sequences have been changed to remove these Shine-Dalgarno-like sequences. These changes eliminate expression of the internal initiation product but do not alter the amino acid sequence of the full length sCD4-PE40 protein. Other similar alterations in sequences in this area will be readily apparent to those skilled in the art.

The present invention is exemplified in more detail in the examples below.

EXAMPLE 1

In this example, we set forth the construction of cells and their induction to express sCD4-PE40 in E. coli.

The UC12656 strain of E. coli is used as the host for sCD4-PE40 expression. This strain is derived from NRRL B-18303. The derivation of the NRRL B-18303 strain is described in International Application No. PCT/US88/0038 which is incorporated herein by reference. The UC12656 strain is made in three steps which employ techniques well known to those skilled in the art. First, NRRL B-18303 is crossed with an Hfr strain to replace the rpoH112 allele with rpoH$^+$. In addition this cross removes a Tn10 adjacent to the rpoH locus, and introduces the rpsL100 allele. Second, the NRRL B-18303 culture is resistant to lambda owing to an alteration in its lamB gene; a lamB$^+$ allele is transduced into the strain. Finally, a cryptic lambda lysogen from the strain TAP106 (obtained from Dr. Donald Court, NCI-Frederick Cancer Institute, Frederick, Md. 21701; Chen, S., et al. (1990) "Expression and characterization of RNaseIII and Era proteins: Products of the rnc operon of *Escherichia coli*." J. Biol. Chem 265:2888–1895) is P1 transduced into the strain to create UC12657. The lambda cryptic from TAP106 contains the following genetic configuration: (intral)▲, N::Kan, cI857, (cro-bioA)▲.

A vector used to express the sCD4-PE40 protein is pUC1456. The vector is derived from pBR322 (available from Pharmacia LKB Biotechnologies, Piscataway, N.J. 08854) by cloning into the EcoRI and HindIII restriction sites a fragment containing the lambda $P_L$ promoter, the TAT32 ribosome binding site, and the sCD4-PE40 gene. The $P_L$ promoter is taken from the pJL-6 vector (Lautenberger, J., et al. (1983) "High-level expression in *Escherichia coli* of the carboxyl-terminal sequence of the avian myelocytomatosis virus (MC29) v-myc protein." Gene:75–84; the vector can be obtained from Dr. Donald Court). The promoter, ribosome binding site and the sCD4-PE40 gene are constructed and cloned using techniques that are well known to those skilled in the art. The $P_L$ promoter is modified by introducing an XbaI restriction site shortly after the +1 nucleotide of the promoter. The modified promoter is designated $P_{L6m}$. The TAT32 ribosome binding site is derived from synthetic oligonucleotides that contained a sequence derived from the ribosome binding site of the bacteriophage T4 gene 32 (Gorski, K., et al. (1985) "The stability of bacteriophage T4 gene 32 mRNA: A 5' leader sequence that can stabilize mRNA transcripts." Cell 43:461–469). The sCD4-PE40 gene is obtained from Chaudhary, V., supra, and modified by making changes in codon usage for several N-terminal codons. The codons that correspond to the N-terminal portion of the protein are modified as described for sCD4 in PCT Application No. PCT/US90/01367.

The pUC1456 vector is transformed into competent cells of UC12656. The culture is developed from one of the transformed colonies and is designated UC12575.

UC12575 cells are grown at 30° C. and induced by heat shifting to 40° C. This results in the formation of intracellular aggregates (inclusion bodies) containing sCD4-PE40.

The vector pUC1456 and transformed culture UC12575 of Example 1 were deposited at The Agricultural Research Culture Collection (NRRL), Northern Regional Research Center, 1815 North University Street, Peoria, Ill. 61604, under the Accession No. NRRL B-18667 on Jun. 27, 1990, in accordance with the requirements of the Budapest Treaty on the International Recognition of the Deposit of Microorganisms for the Purposes of Patent Procedure.

EXAMPLE 2

This example describes the isolation and characterization of the impurity that contaminates preparations of sCD4-PE40.

Samples containing sCD4-PE40 in inclusion body form are analyzed by SDS-polyacrylamide gel electrophoresis (SDS-PAGE), electroblotting on PVDF membranes, Western blotting, and sequencing according to methods readily apparent to those skilled in the art. In particular, the solids from cells or inclusion body preparations are collected by centrifugation. SDS-PAGE is performed essentially as described by Laemmli (Laemmli, U. (1970) "Cleavage of structural proteins during the assembly of the head of bacteriophage T4." Nature 227:680–685), except that samples are heated at 100° C. for 5 minutes in ethanolamine sample buffer (10 g SDS; 45 ml water, 20 ml 1M ethanolamine, pH 10; 25 ml glycerol; 10 ml 0.05% (w/v) Bromophenol Blue) for five minutes before application to gels. Following electrophoresis, these gels are rinsed immediately, arranged in a blotting sandwich containing polyvinylidine difluoride (PVDF) membranes (Immobilon, pore size 0.45 μm), and blotted electrophoretically. This protein transfer to the PVDF membrane is by the discontinuous semi-dry method of Hirano, H. (1989) "Microsequence analysis of winged bean seed proteins electroblotted from two-dimensional gel." J. Protein Chem. 8(1):115–130. The blots are either visualized with anti-sera or with Coomassie Blue R250.

SDS-PAGE analysis of cells expressing sCD4-PE40 reveals a major band at about 60,000 daltons corresponding to the recombinant product as well as a variety of other bands. When the inclusion bodies are separated from soluble proteins, the sCD4-PE40 is enriched, increasing from 10–20% of the total protein to 50–80%. The major impurity band, which has an apparent weight of about 50,000 daltons, is also greatly enriched. By densitometric scanning, this band is 5–20% of the sCD4-PE40 band.

Western analysis of the PVDF blots is conducted to determine if the observed bands are related to sCD4-PE40. Immunodetection is accomplished with rabbit anti-sera to sCD4-183, to sCD4-PE40, and to Lys-PE40 (Domains 2 and 3 of Pseudomonas exotoxin A). Many immunoreactive bands are observed, including the major impurity. The band with an apparent weight of 50,000 daltons is immunoreactive with each antibody tested, indicating that it contains domains of both sCD4 and PE40.

For N-terminal sequence analysis, the PVDF membranes containing the blotted protein are stained with Coomassie Blue R250 for 2 minutes, destained with an aqueous solution of 50% methanol and 10% acetic acid for 3 minutes, rinsed with Milli-Q water and air dried. The 50 Kd protein band is excised from the dried blot, cut into approximately 2×4 mm pieces, and loaded into the upper block of a sequencer cartridge above a Polybrene-loaded, precycled filter. N-terminal sequence analysis is performed on an Applied Biosystems (ABI) 470A sequencer equipped with an on-line ABI 120A PTH analyzer.

Following SDS-PAGE of sCD4-PE40 from inclusion bodies, the 50,000 dalton impurity located with Coomassie Blue R-250 on a PVDF membrane was sequenced through residues on the ABI 470A. Two sequences were apparent, with the minor species presumably representing cross-contamination by the neighboring 60,000 dalton band since it had the N-terminus of sCD4-PE40 (e.g., Met$^1$-Lys$^2$-Lys$^3$-Val$^4$-Val$^5$-Leu$^6$-Gly$^7$). The most abundant sequence begins with Met-Leu-Val-Phe-Gly-Leu-Thr-Ala, corresponding to N-terminal methionine followed by Leu$^{97}$ through Leu$^{110}$ of sCD4-PE40.

EXAMPLE 3

In this example, we set forth the design and construction of a synthetic DNA fragment from oligonucleotides to eliminate a Shine-Dalgarno-like sequence in sCD4-PE40.

The DNA sequence between the BclI and EcoNI restriction sites of the cDNA encoding sCD4-PE40 is shown below. These restriction sites are unique for the CD4-PE40 gene. The BclI-EcoNI fragment encompasses codons 71 (ATC) through 111 (CAG) of the sCD4-PE40 sequence, which corresponds to codons 72–112 in the cDNA sequence determined by Maddon, supra.

```
BclI
TG  ATC ATC AAG AAT CTT AAG ATA GAA GAC TCA GAT ACT TAC ATC TGT GAA
    Ile Ile Lys Asn Leu Lys Ile Glu Asp Ser Asp Thr Tyr Ile Cys Glu

96
GTG GAG GAC CAG AAG GAG GAG GTG CAA TTG CTA GTG TTC GGA TTG ACT GCC AAC
Val Glu Asp Gln Lys Glu Glu Val Gln Leu Leu Val Phe Gly Leu Thr Ala Asn

EcoNI
TCT GAC ACC CAC CTG CTT CAG G
Ser Asp Thr His Leu Leu Gln
```

In the sequence preceding the codon for amino acid 96 there are three regions that have strong homology to the so-called Shine-Dalgarno sequence (e.g. a sequence complementary to the 3' end of the 16s rRNA) and could be used as ribosome binding sites. These sequences are indicated below:

```
                                                              96
AT ACT TAC ATC TGT GAA GTG GAG GAC CAG AAG GAG GAG GTG CAA TTG
                                                              96
AT ACT TAC ATC TGT GAA GTGGAG GAC CAG AAG GAG GAG GTG CAA TTG
                                                              96
AT ACT TAC ATC TGT GAA GTG GAG GAC CAG AAG AGA GAG GTG CAA TTG
```

To disrupt these Shine-Dalgarno-like sequences the following base substitutions can be made without altering the amino acid sequence of the encoded protein.

```
                                      GAA GAA              96
AT ACT TAC ATC TGT GAA GTG GAG GAC CAG AAG GAG GAG GTG CAA TTG
                                      AAA GAA              96
AT ACT TAC ATC TGT GAA GTGGAG GAC CAG AAG GAG GAG GTG CAA TTG
                                GTT GAA                    96
AT ACT TAC ATC TGT GAA GTG GAG GAC CAG AAG AGA GAG GTG CAA TTG
```

In addition the TTG initiation codon can be changed from TTG to CTG. The CTG codon is not a known initiation codon. Additional codon changes have been made in the DNA sequence to optimize the codon usage in this region. The use of codon optimization is known to those skilled in the art. These changes are shown above the native sequence.

```
BclI            AAC CTG     ATC         TCT     ACC
TG  ATC ATC AAG AAT CTT AAG ATA GAA GAC TCA GAT ACT TAC ATC TGT GAA
    Ile Ile Lys Asn Leu Lys Ile Glu Asp Ser Asp Thr Tyr Ile Cys Glu

GTT     CTG     TTT GGT CTG     GCT
GTG GAG GAC CAG AAG GAG GAG GTG CAA TTG CTA GTG TTC GGA TTG ACT GCC AAC
Val Glu Asp Gln Lys Glu Glu Val Gln Leu Leu Val Phe Gly Leu Thr Ala Asn

ACT   EcoNI
TCT GAC ACC CAC CTGCTT CAG G
Ser Asp Thr His Leu Leu Gln
```

The codon optimization changes in combination with the codon change for removal of the three ribosome binding sites and the TTG initiation site are shown as a composite below. The codon changes are indicated above the native sequence.

```
BclI            AAC CTG     ATC         TCT     ACC
TG ATC ATC AAG AAT CTT AAG ATA GAA GAC TCA GAT ACT TAC ATC TGT GAA
   Ile Ile Lys Asn Leu Lys Ile Glu Asp Ser Asp Thr Tyr Ile Cys Glu

GTT GAA         AAA GAA GAA GTT     CTG CTG     TTT GGT CTG     GCT
GTG GAG GAC CAG AAG GAG GAG GTG CAA TTG CTA GTG TTC GGA TTG ACT GCC
Val Glu Asp Gln Lys Glu Glu Val Gln Leu Leu Val Phe Gly Leu Thr Ala

ACT     EcoNI
AAC TCT GAC ACC CAC CTG CTT CAG G
Asn Ser Asp Thr His Leu Leu Gln
```

Four oligonucleotides are synthesized as described in International Application No. PCT/US88/00328 which is incorporated herein by reference. These oligonucleotides, when hybridized and ligated, will form a synthetic fragment that contains the codon changes presented above and can be cloned into the unique BclI/EcoNI sites of the CD4-PE40 gene thus replacing the native sequence that contains the intragenic ribosome binding site. The sequences of the four oligonucleotides are:

1. 5' GATCATCAAGAACCTGAAGATCGAAGACTCTGATACCTACATCTGTGAAGTTGAAGA
2. 5' CCAGAAAGAAGAAGTTCAACTGCTGGTGTTTGGTCTGACTGCTAACTCTGACACTCACCTGC
3. 5' AGCAGGTGAGTGTCAGAGTTAGCAGTCAGACCAAACACCAGCAGTTGAACTTCTTCT
4. 5' TTCTGGTCTTCAACTTCACAGATGTAGGTATCAGAGTCCTTCGATCTTCAGGTTCTTGAT

The crude oligonucleotides are purified by cutting out the product band on a 20% acrylamide gel and desalting over a Waters Sep-Pak column as described in PCT Application No. PCT/US88/00328. The oligonucleotides form strands of the synthetic fragment as indicated below.

```
5'   1     2     4     3   5'
```

The procedures used can found in *Current Protocols in Molecular Biology* (edited by Ausubel, F., et al., and published by John Wiley and Sons). Oligonucleotides 2 and 4 are kinased using $^{32}$P gamma labeled ATP. Oligonucleotides 1 and 4, and 2 and 3 are hybridized to each other. The two set of hybridized oligonucleotides 1/4 and 2/3 are ligased and run on a 12% acrylamide gel. The synthetic oligonucleotide derived DNA fragment is visualized by autoradiograph, cut from the gel and isolated. The sequence of the synthetic DNA fragment is as follows:

pUC1456 vector is transformed into the *E. coli* strain CGSC 6580 which had been lysogenized with the bacteriophage lambda. This strain carries the dam13::Tn9 allele (the strain can be obtained from Dr. Barbara Bachmann, Coli Genetic Stock Center, Department of Biology, 255 OML, Yale University, P.O. Box 6666, New Haven, Conn. 06511-7444). The dam13::Tn9 allele prevents methylation of the adenine in the sequence GATC. Methylation of this site prevents the BclI restriction enzyme from cutting the DNA. The use of dam deficient host to permit the BclI enzyme to cut is well known to those skilled in the art. Vector DNA is isolated and digested with BclI and EcoNI restriction endonucleases. This digestion produces a large vector fragment, a 1837 bp fragment and a 115 bp fragment. The vector fragment is isolated from an agarose gel, and is ligated to the synthetic oligonucleotide derived fragment and transformed into competent cells of UC12656. The juncture formed between the EcoNI site of the oligonucleotide derived fragment of Example 3 and the EcoNI site in the vector generates a PstI restriction site which can be used to identify candidates with the oligonucleotide fragment inserted. One of the candidates identified by restriction analysis is selected and the presence of the oligonucleotide fragment insert is confirmed by DNA sequence analysis. The vector is designated pUC1470.

In order to reconstruct the sCD4-PE40 gene an additional vector pUC1469 is constructed. The pBR322 vector contains EcoRI, ClaI, HindIII, EcoNI and NdeI restriction sites. Each one of these sites are unique in the vector. The

```
BclI
5' GATCATCAAGAACCTGAAGATCGAAGACTCTGATACCTACATCTGTGAAGTTGAAGACCAGAAAGAAGAA
     TAGTTCTTGGAGTTCTAGCTTCTGAGACTATGGATGTAGACACTTCAACTTCTGGTCTTTCTTCTT
                                                                EcoNI
   GTTCAACTGCTGGTGTTTGGTCTGACTGCTAACTCTGACACTCACCTGC
   CAAGTTGACGACCACAAACCAGACTGACGATTGAGACTGTGAGTGGACGA 5'
```

EXAMPLE 4

In this example we set forth the cloning of the BclI/EcoNI fragment into the CD4-PE40 gene.

A detailed description of the cloning methodologies employed herein can be found in *Current Protocols in Molecular Biology* (supra). These techniques and the pBR322 vector use in the clonings described are well known to those skilled in the art.

The pUC1456 vector described in Example 1 contains BclI and EcoNI restriction sites in the sCD4-PE40 gene and a second EcoNI restriction site resident in the pBR322 sequence downstream of the HindIII restriction site. The CD4-PE40 gene can be cloned as a ClaI/HindIII fragment into the corresponding ClaI/HindIII restriction site in the pBR322 vector. However, in such a vector the EcoNI site in the CD4-PE40 gene would not be unique. To prevent this the pBR322 vector is cut with the HindIII and NdeI restriction enzymes. The "sticky" ends are filled with PolA Klenow fragment in the presence of dNTPs. The DNA is run on an agarose gel and the fragment containing the ampicillin resistance gene and origin of replication is isolated, ligated and transformed into competent cells of MC1061. Candidates are analyzed by restriction digestion, and a clone with the deletion identified. The ligation of the HindIII and NdeI restriction sites regenerates a HindIII site. This vector is designated pUC1468. The ClaI/HindIII CD4-PE40 fragment is isolated from pUC1456 and is cloned into the pUC1468 vector at the corresponding ClaI/HindIII sites. The resultant vector is designated pUC1469.

To regenerate the sCD4-PE40 gene, the pUC1470 vector is digested with EcoNI and EcoRI restriction enzymes and a fragment of approximately 600 bp containing the $P_{L6m}$ promoter, the TAT32 ribosome-binding site and the 5' portion of the sCD4-PE40 gene with the modifications of the internal ribosome-binding sites is isolated. The pUC1469 vector is digested with EcoRI and EcoNI restriction enzymes to generate a vector fragment and a fragment of approximately 600 bp. The vector fragment is isolated. The two isolated fragments are ligated and transformed into UC12656. The DNA sequence derived from the oligonucleotide fragment contains an XmnI site that can be used for characterizing clones. A candidate with the correct restriction analysis is identified. The sequence modified by the cloning of the oligonucleotide fragment is sequenced for confirmation. The resultant vector is designated pUC1467. This vector is transformed into UC12656, and the resultant culture, designated UC12657, is capable of high level expression of the unmodified sCD4-PE40 protein from the modified gene. The vector pUC1467 and transformed culture UC12657 of Example 4 were deposited at The Agricultural Research Culture Collection (NRRL), Northern Regional Research Center, 1815 North University Street, Peoria, Ill. 61604, under the Accession No. NRRL B-18676 on Jul. 13, 1990, in accordance with the requirements of the Budapest Treaty on the International Recognition of the Deposit of Microorganisms for the Purposes of Patent Procedure.

EXAMPLE 5

In this example, it is shown that the use of a modified gene, such as described in Example 4, eliminates the production of the 50 kilodalton fragment which was described in Example 2.

Strain UC12657 containing pUC1467 is grown and induced as described for strain UC12575 in Example 1. The cells are analyzed for sCD4-PE40 using SDS-PAGE and Western blotting as described in Example 2. An examination of the gel reveals the 50 kilodalton, immunoreactive species apparent in the UC12575 culture is not detected in the induced UC12657, indicating that internal initiation has been eliminated.

We claim:

1. An expression vector comprising the following elements in operable linkage: the $P_{L6m}$ promoter, the TAT32 ribosome binding site and a gene encoding a heterologous polypeptide.

2. The expression vector of claim 1 wherein the gene encodes sCD4-PE40.

3. The expression vector of claim 1 which is pUC1456.

4. An *E. coli* host cell transformed with the expression vector of claim 1.

5. An *E. coli* host cell transformed with pUC 1456.

6. The *E. coli* host cell of claim 5 that is UC12575 (NRRL B-18667).

* * * * *